United States Patent [19]
Washer

[11] Patent Number: 5,828,307
[45] Date of Patent: Oct. 27, 1998

[54] HYDROCARBON GAS MONITOR DESK

[75] Inventor: Tom J. Washer, Borger, Tex.

[73] Assignee: Phillips Petroleum Company, Bartlesville, Okla.

[21] Appl. No.: 700,346

[22] Filed: Sep. 23, 1996

[51] Int. Cl.⁶ .................................................. G08B 17/10
[52] U.S. Cl. ........................ 340/632; 307/118; 307/140; 361/683; 200/61.03
[58] Field of Search .............................. 340/632; 73/23.2; 200/61.03; 361/683, 727; 307/116, 117, 118, 139, 140

[56] References Cited

U.S. PATENT DOCUMENTS

| | | | |
|---|---|---|---|
| 4,065,653 | 12/1977 | Jones | 200/302 |
| 4,251,727 | 2/1981 | Piercy | 250/343 |
| 4,422,859 | 12/1983 | McGee | 55/16 |
| 5,358,429 | 10/1994 | Mina | 439/695 |
| 5,430,607 | 7/1995 | Smith | 361/683 |

FOREIGN PATENT DOCUMENTS 268107  9/1993  European Pat. Off. .

*Primary Examiner*—Jeffery A. Hofsass
*Assistant Examiner*—Julie Lieu
*Attorney, Agent, or Firm*—George E. Bogatie

[57] ABSTRACT

An enclosure for housing electrical equipment is constructed to simplify use of general purpose electrical equipment at a location in a petroleum refinery which may contain combustible vapors. The construction provides an enclosure that is vapor tight except for an open front, thus providing user access and adequate ventilation to equipment such as a computer. In use a combustible gas monitor surveys the relatively small open area at the front of the enclosure and automatically disconnects electric current supplied to the general purpose rated equipment inside the enclosure on detection of a dangerous concentration of combustible gas entering through the front opening.

5 Claims, 3 Drawing Sheets

HYDROCARBON GAS MONITOR DESK

This invention relates to use of a combustible gas monitor for testing atmosphere at a petroleum facility. More particularly it relates to general purpose rated electrical equipment for use in an area designated as hazardous according to a national or local government electrical safety code.

BACKGROUND OF THE INVENTION

Electrical power supplied to the point of entry into an electrical instrument in a hazardous location is subject to detailed rules and regulations. In most of the United States the "Recommended Practice for Classification of Locations for Electrical Installations at Petroleum Facilities" issued by the American Petroleum Institute has been adopted by petroleum facilities.

One method of safely operating electrical instruments suggested by the code is to prevent combustible gases from contacting any instrument that could create an arc or have a thermal storage sufficient to ignite the combustible gas. This method is usually accomplished by maintaining a slight positive pressure of air or inert gas within the enclosure so that hazardous or otherwise contaminated atmosphere cannot enter. While this method is applicable to any size or type of equipment and can be applied to large enclosures, thus avoiding possible excessive temperatures inside small purged enclosures with inadequate ventilation, it is relatively expensive and difficult to maintain for an entire building such as some control houses.

It is also known, and permissible according to the code, to detect potentially explosive concentrations of methane, ethane, propane, butane and other hydrocarbon gases using infrared monitors that can provide alarm signals for automatically shutting down low thermal storage electrical equipment in the event a combustible gas is encountered. As used herein, low thermal storage equipment is equipment having electrical power supplied from a single source and containing no accessible electrical parts that may operate at a temperature equal to or above eighty percent of the ignition temperature of the gas or vapor involved. This method also has disadvantages for monitoring entire buildings, such as some control houses, because an adequate number of sensors must be installed and carefully positioned to ensure the sensing of combustible gas in all areas where such gas might accumulate.

Accordingly, it is an object of the present invention to construct an enclosure for electrical equipment that simplifies reliable detection of combustible gases by a gas monitor.

Another object of this invention is to safely operate low thermal storage electrical equipment rated for a general purpose location in a hazardous location (class 1, Division 2) of a petroleum/chemical processing facility or laboratory.

Yet another object is to provide an electrical apparatus for use in a location designated as hazardous by a national or local government safety code.

A more specific object is to provide control room operators in a refinery with a personal type computer for communication, data modification, data retrieval, graphic displays, calculations, etc.

SUMMARY OF THE INVENTION

According to the present invention, the foregoing and other objects and advantages are attained by constructing an enclosure for electrical equipment that allows effective use of a combustible gas monitor. The enclosure is essentially vapor tight except for a front access opening. Inside the enclosure the combustible gas monitor and other electrical equipment are sheltered from the outside atmosphere, and the gas monitor is securely mounted and positioned to monitor any atmosphere entering through the front opening. The gas monitor is safety rated for operation in the hazardous location, and provides an alarm signal in the event combustible gas is detected. Other electrical equipment inside the enclosure is low thermal storage electrical equipment, safety rated for general purpose locations, and a power disconnecting circuit having associated relay contacts separately enclosed in an explosion-proof box. Electric power, provided by wiring suitable for class 1, Division 2 hazardous locations, is supplied directly to the gas detector and the power disconnecting circuit, and supplied to the other electrical equipment through an electrical power outlet strip mounted in the enclosure. Activation of the alarm signal in cooperation with the power disconnecting circuit automatically disconnects current to the receptacle.

In a preferred embodiment the enclosure includes two adjoining vapor tight compartments, with one compartment containing a gas detector having dual sensor heads, a computer, a printer, a keyboard, a CRT, power outlet strips, a circuit breaker and a power disconnecting circuit. The second compartment contains, power outlet strips, and miscellaneous equipment such a radio, a battery charger, etc.

The method and apparatus of the invention using the combustible gas monitor thus surveys only a relatively small area defined by the front opening for protecting a relatively large volume containing electrical equipment inside the enclosure. The probability of failing to detect an accumulation of combustible gas that could contact the general purpose rated equipment is relatively remote.

Other objects and advantages of the invention will be apparent to those of ordinary skill in the art from the foregoing brief description of the invention and the claims as well as the accompanying figures which illustrate the preferred embodiment of the present invention.

DETAILED DESCRIPTION OF PREFERRED EMBODIMENT

The invention is described in terms of a combustible gas monitor having two sensor heads for monitoring hydrocarbon gases in an indoor area that could at one time or another contain combustible vapors. The hydrocarbon sensors are of the type responding to contact with the combustible gas and the sensors are mounted on a partition that divides the enclosure. The environment contemplated for use of the invention is indoors at a petroleum refinery, however, the invention is not limited to this environment, type of sensor, or placement of the of sensor employed, since it would be within the ability of a person skilled in the chemical art to position a different type of sensor in a different location while achieving the results of the present invention.

Figure 1:
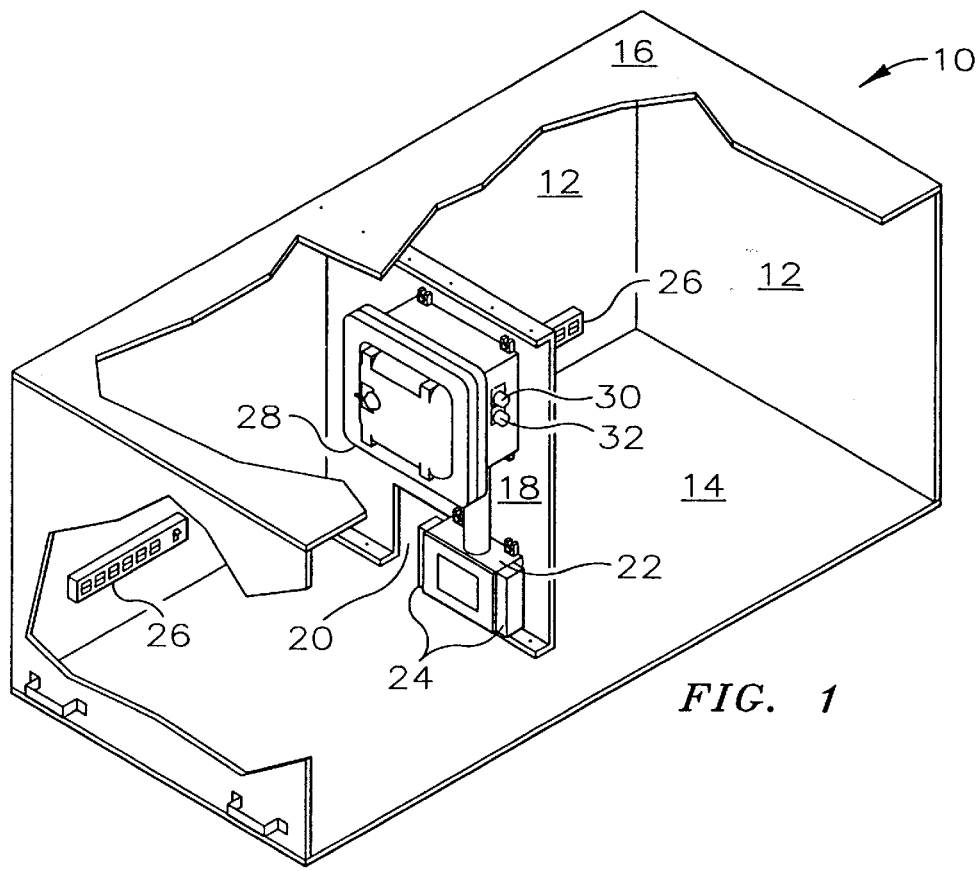
FIG. 1 is a perspective view of an electrical enclosure partially cut away to show location of the gas monitor with associated sensor heads, and a power disconnecting circuit contained in an explosion-proof box.
Figure 2:
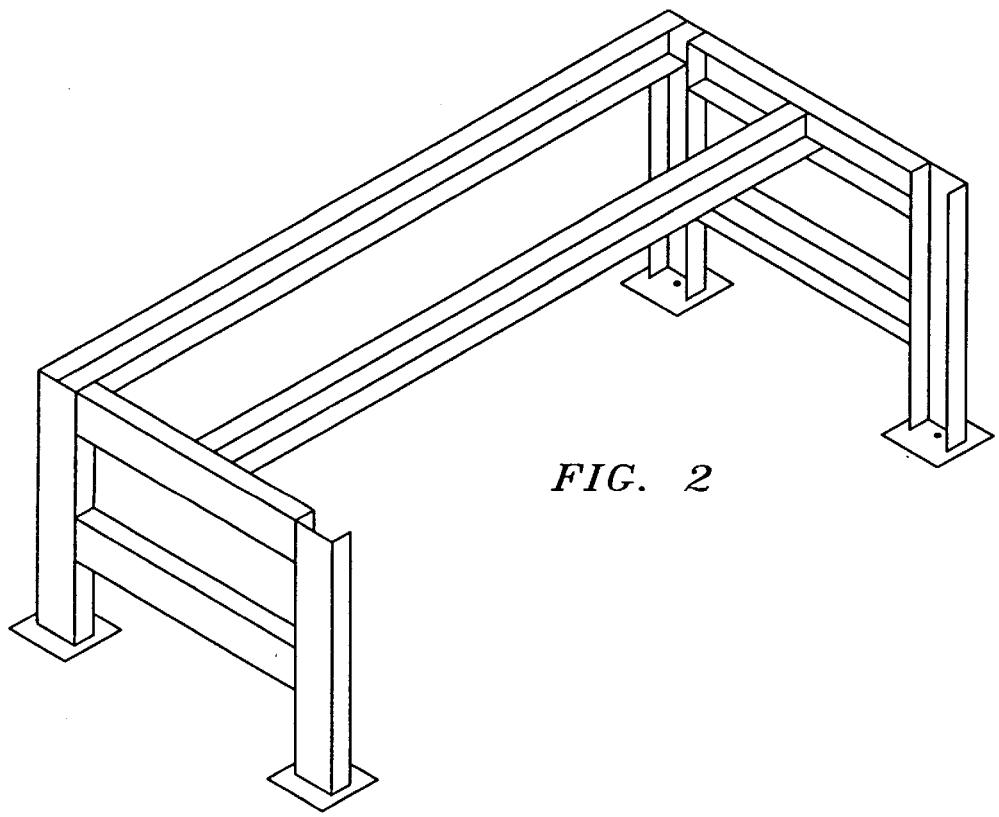
FIG. 2 is a perspective view of a base for supporting the enclosure of FIG. 1.

Referring now to FIG. 1 of the drawings, a typical electrical enclosure is generally illustrated at 10. The enclosure, which is illustrated without general purpose rated equipment installed, includes walls 12, a floor 14, a ceiling 16, shown partially cut away to reveal location of the partition 18. Preferably the enclosure is constructed of aluminum, and completely closed except for the open front. An important consideration for construction of the enclosure is providing resistance to air or vapor flow through any of the ceiling, wall and floor joints. Accordingly, all of the joints are sealed by any suitable means such as caulking or welding. Partition 18 divides the enclosure 10 into two compartments, and further provides an opening adjacent to the floor 14, as illustrated at 20.

Securely mounted on the partition 18 is the combustible gas monitor 22 having a pair of sensor heads illustrated at 24. The sensor heads may be mounted at any desired position in the enclosure 10, and any number of sensor heads may be utilized. The important consideration is selecting a location most likely to first contact any combustible gas present in an atmosphere that may enter the front opening of the enclosure 10. As shown in FIG. 1, one sensor head is mounted toward the front of the enclosure 10, and a second sensor is mounted adjacent the opening 20 in the partition 18. Another possible mounting location for a sensor head 24 is underside of the ceiling towards the open front of the enclosure 10. Preferably positioning of partition 18 is field adjustable such that the sensor heads 24 may easily be moved toward or away from the open front. Also the partition 18 may be moved toward either sidewall 12 to accommodate various arrangements of equipment. A generally preferred position places the front sensor head 24 about eight inches inside the enclosure. This position is effective for sensing gases while avoiding accidental contact with control room personnel. Also mounted on the partition 18 is the explosion proof box 28 containing the power disconnecting circuit, which will be explained more fully hereinafter. Two warning lights associated with the power disconnecting circuit are indicated at 30 and 32 on the box 28. All penetrations of the enclosure 10 by field wiring or power cords are sealed using silicon rubber caulk or equal, thus providing a construction that is vapor tight except for the front opening.

Figure 3:
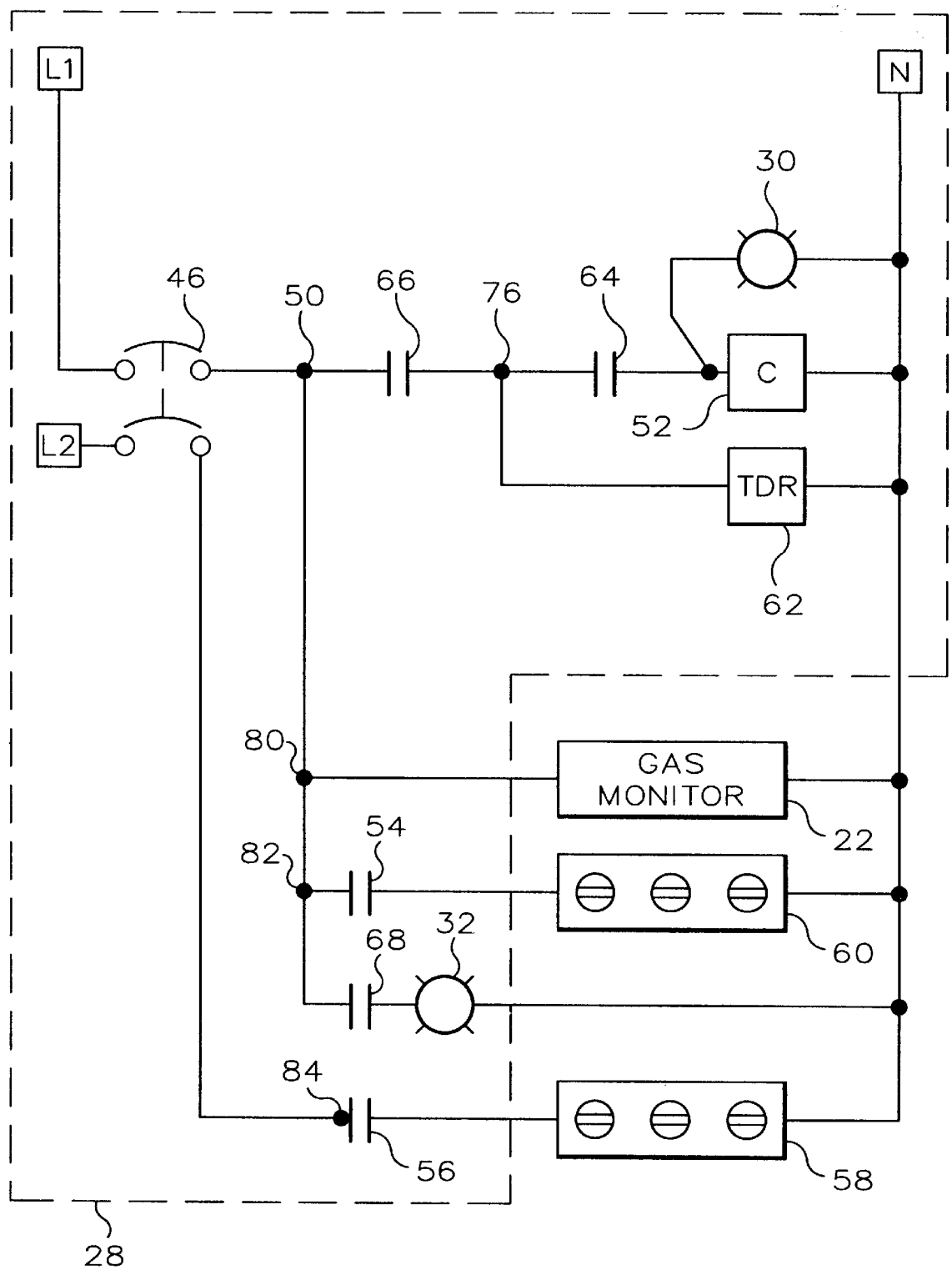
FIG. 3 is an electrical schematic diagram showing the power disconnecting circuit according to this invention.

The gas monitor 22 is rated for class 1 division 2 locations and will not deenergize on an alarm condition that causes a shutdown of the general purpose equipment. It cooperates with the power disconnecting circuit to provide the automatic shutdown and alarm indication if the vapor detected reaches e.g., a 20 percent lower flammable limit. A thirty second time delay period must lapse before power strips 26 are reenergized after the gas monitor clears a shutdown alarm and is manually reset. The same 30 second lapse will occur if the power is interrupted as would occur during a utility power failure, or by manual operation of the circuit breaker 46. This delay is to allow time for the gas monitor to survey for a combustible level of vapor prior to reenergizing the power strips, thus preventing the strips from being reenergized in the presence of combustible gas. FIG. 3 is an electrical schematic wiring diagram showing the gas monitor 22 and the power disconnecting circuit that includes several electrical relay contacts. In accordance with recommended safety practice all contacts are contained in an explosion proof box (NEMA-7) indicated by the dash line 28 in FIG. 3. The power disconnecting circuit includes a contactor 52 with associated contacts 54 and 56, power outlet strips 58 and 60, time delay relay 62 with associated contact 64, and contacts 66 and 68 associated with the gas monitor 22, indicator lights 30 and 32, circuit breaker 46, and power terminals L1, L2 and N. An additional safety feature is provided by the monitor 22 in that contact 66 must be manually set to the closed position by a reset switch (not illustrated) of the gas monitor 22. Alternately the contact 66 can be reset by operating the ON/OFF position of circuit breaker 46.

Referring now specifically to FIG. 3, three wire single phase AC voltage is supplied from an external source to terminals L1, L2, and N. Preferably the voltage is 240 volts L1 to L2, and 120 volts L1 or L2 to the neutral wire N, as is commonly supplied to commercial facilities. As is standard practice, a circuit breaker 46 is provided to automatically interrupt current under infrequent abnormal conditions. As shown in FIG. 3, line L1 extends through circuit breaker 46 and provides its voltage on junction points 50, 80 and 82. Likewise line L2 extends through circuit breaker 46 and provides its voltage to terminal 84 on contact 56. Line N extends throughout the circuit, and can be considered a common junction point for return of current supplied by L1 and L2. Accordingly, L1 supplies current through various contacts to the contactor 52, time delay relay 62, power outlet strip 60, indicator lights 30 and 32 and further directly powers the gas monitor 22. Line L2 supplies current to power outlet strip 58.

Still referring to FIG. 3 operation of the circuit proceeds as follows: without power applied all contacts are normally open. Closing circuit breaker 46 applies power to the gas monitor 22, and assuming normal conditions of a clear state for combustible gas, power is applied to contact 66, which is connected between junctions 50 and 76, and contact 68 connected between junction 82 and one terminal of indicator light 30. Closing contact 66 applies power to the solenoid of time delay relay (TDR) 62, which is connected between junction 76 and the neutral line N. On lapse of a thirty second time delay, TDR closes contact 64 which applies power to contactor 52. Contactor 52, which is essentially a heavy duty relay to control electric power circuits, closes contacts 54 and 56 to supply current to power outlet strips 60 and 58 respectively. Indicator light 72 is connected in parallel with the solenoid of contactor 52 and accordingly follows the voltage applied to the solenoid 52. In normal operation both indicator lights 30 and 32 are illuminated.

Indicator light 32 is an amber colored warning light, and is extinguished responsive to the gas monitor opening contact 68 on sensing a trace level of combustible gas. If the vapor detected by gas monitor 22 reaches 20 percent of the lower flammable limit, contact 66 opens thus interrupting current to the contactor 52, and in turn opening contacts 54 and 56 disconnecting power to the power outlet strips 58 and 60. In this manner all equipment in the enclosure 10 is disconnected from its supply of electric current except for the gas detector 22. On clearing of the combustible condition and manually resetting the contact 66, power is returned to the power outlet strips after lapse of the time delay associated with relay 62.

The invention has been described in terms of a preferred embodiment as illustrated in FIG. 1 and 3. Specific components used in the practice of this invention as shown in FIG. 3 such as the gas detector 22, contactor 52, time delay relay 62 and power outlet strips 58 and 60 are each well known commercially available components, available from vendors. Examples of suitable components are illustrated in the following table.

| Description | Manufacture | Catalog |
|---|---|---|
| Hydrocarbon Gas Detector | General Monitor Lake Forest, California | IR 2000-321-101-701 |
| Time Delay Relay | Potter Brumfield Princeton, Indiana | CDA-38-70028 |
| Circuit Breaker | Westinghouse | EHD 2030L |
| Contacter | Square D | 8501-C016\120 |
| Power Outlet Strips (6 outlets) | Intermatic | 1G11266 |

Figure 4:
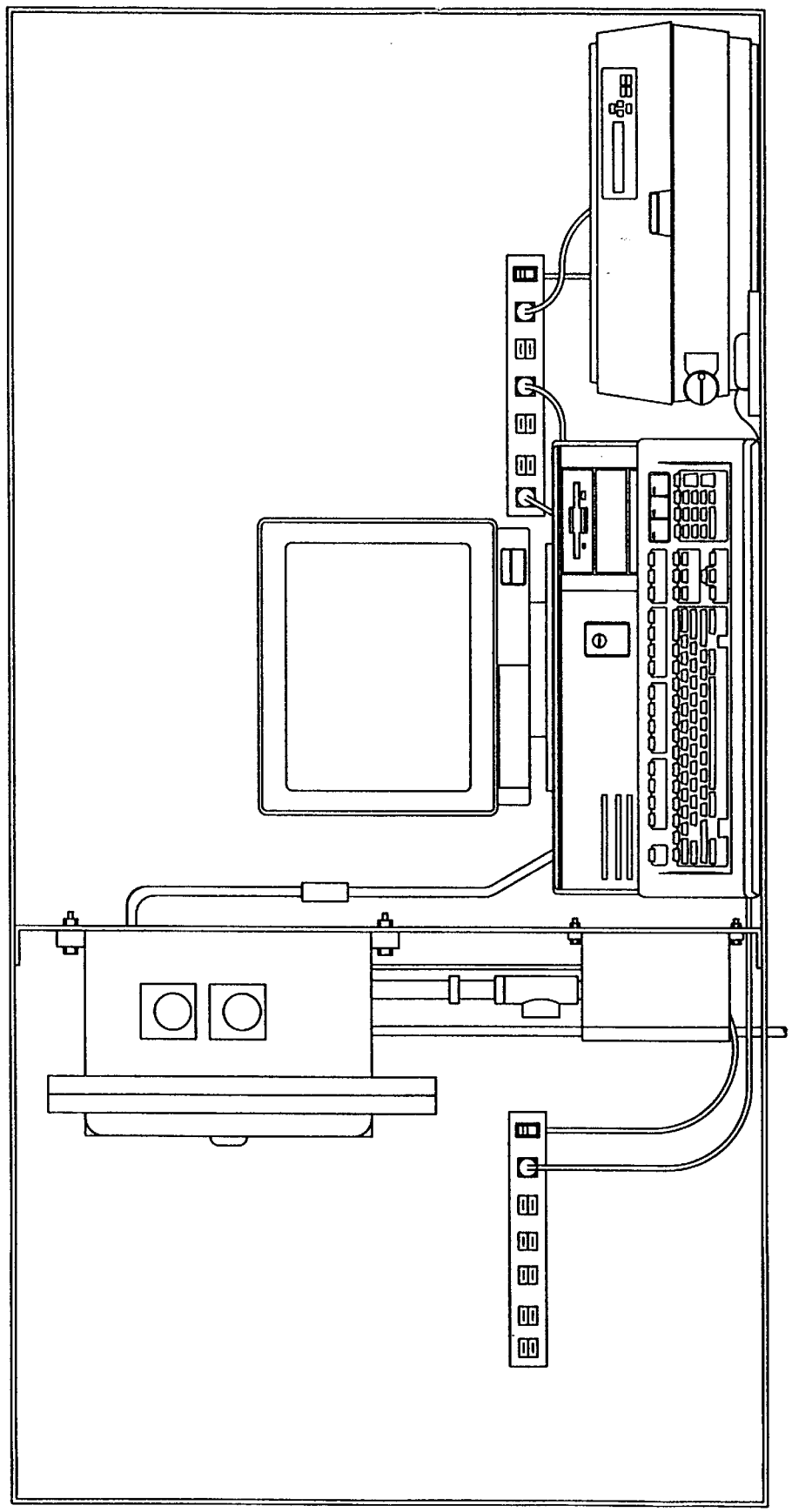
FIG. 4 is a perspective view of the electrical enclosure having equipment located therein according to this invention.

Accordingly, there have been described an apparatus and method for effective use of a gas monitor to simplify use of electrical equipment, that is safety rated for general purpose locations, in a location at a refinery where hydrocarbon gases such as methane, ethane, etc., might accumulate to cause a dangerous condition. The general purpose equipment is housed in a vapor tight enclosure except for a front opening that is surveyed by the gas monitor. The construction of the enclosure thus directs any hazardous vapor that may be present, as in a class 1, division 2 area, to be detected before vapor concentration reaches a dangerous combustible level, which could be ignited by general purpose rated electrical equipment, such as a computer, printer, etc. If combustible gas is detected, all general purpose electrical equipment in the enclosure, as illustrated in FIG. 4, is automatically de-energized. The internal volume of the electrical enclosure is at least two orders of magnitude smaller than the control house in which it is located. Therefore, relative speed of gas detection and safe deenergization of general purpose equipment is enhanced for a given number of gas sensors. In the preferred arrangement of sensor heads in the enclosure, all general purpose equipment in the enclosure is less than 5½ feet away from a gas monitor sensor head. In use, the combustible gas monitor surveys only the relatively small frontal open area, and on detecting vapor exceeding 20 percent of its lower flammable limit, it will alarm and automatically activate the power disconnecting circuit contained in the Nema 7 explosion proof box. Consequently, all general purpose rated electrical equipment in the enclosure is deenergized before exposure to combustible gases that could be ignited by the equipment.

In this disclosure, there is shown and described only the preferred embodiment of the invention, but as mentioned above, it is to be understood that this invention is adaptable to for use in various other conditions and environments, and it will be appreciated that certain changes and modifications can be made without departing from the spirit of the invention as expressed in the appended claims.

That which is claimed:

1. Apparatus for use in an area designated as hazardous according to a national or local government electric code, said apparatus comprising:
   (a) an electrical enclosure having a construction that is essentially vapor tight except for a front access opening, said enclosure including:
      i. an enclosed frame structure having all joints sealed to resist vapor entry;
      ii. a table top surface on said frame structure;
      iii. a compartment located beneath said top surface for containing said gas monitor, said low thermal storage electrical devices and said electrical receptacle; and wherein said compartment includes said front access opening; and
      iv. four legs for supporting said enclosed frame structure,
   (b) a combustible gas monitor for producing an alarm signal on detection of a predefined level of explosive gas concentration;
   (c) wherein said gas monitor is securely mounted in said enclosure and aligned to monitor the atmosphere introduced through said front access opening, and wherein said combustible gas monitor is rated for operation in said hazardous location;
   (d) means for delivering electric current to equipment housed in said enclosure;
   (e) at least one low thermal storage electrical device, which is safety rated for general purpose areas, wherein said device is housed in said electrical enclosure;
   (f) an electrical power receptacle housed in said electrical enclosure for delivering electric current to said at least one low thermal storage device; and
   (g) means responsive to said alarm signal for automatically disconnecting electric current delivered to said at least one low thermal storage electrical devices through said electrical receptacles.

2. Apparatus in accordance with claim 1 additionally comprising:
   a partition adjustably located to divide said compartment into two sections.

3. Apparatus in accordance with claim 1, wherein said means for delivering electric current includes wires designated as L and N for supplying AC electric current, said apparatus additionally comprising:
   a power disconnecting electric circuit having electrical contacts contained in an explosion-proof box mounted within said electrical enclosure, said power disconnecting electric circuit including:
      i) an electric contactor including a solenoid and at least one contact means;
      ii) a time delay relay including a solenoid and at least one contact means;
      iii) means for connecting a series arrangement of said contactor solenoid and said time delay relay contact means between said line N and a first junction point;
      iv) means for connecting the solenoid of said time delay relay between said line N and said first junction point;
      v) means for connecting said gas alarm contact between said first junction point and said line L;
      vi) means for connecting said electrical receptacle between said line N and a second junction point; and
      vii) means for connecting said contact means of said contactor between said second junction point and said line L.

4. A method for using combustible gas monitoring equipment for safely operating low thermal storage electrical devices safety rated as general purpose in a location designated as hazardous according to a national or local government electric code, said method comprising:
   (a) providing an electrical enclosure having a construction that is essentially vapor tight except for a front access opening;
   (b) securely mounting a combustible gas monitor in said electrical enclosure, wherein said combustible gas monitor produces an alarm signal on detection of a predefined level of explosive gas concentration, and wherein said gas monitor is positioned to monitor the atmosphere introduced through said front access opening;
   (c) providing electric current to equipment housed in said electrical enclosure;
   (d) housing at least one low thermal storage electrical device safety rated for general purposes in said electrical enclosure;

(e) providing an electrical receptacle in said electrical enclosure for supplying electrical current to said low thermal storage electrical devices;
(f) providing a power disconnecting circuit separately enclosed for operation in a hazardous location, said power disconnecting circuit comprising:
 i) an electric contactor including a solenoid and at least one contact means;
 ii) a time delay relay including a solenoid and at least one contact means;
 iii) means for connecting a series arrangement of said contactor solenoid and said time delay relay contact means between said line N and a first junction point;
 iv) means for connecting the solenoid of said time delay relay between said line N and said first junction point;
 v) means for connecting said gas alarm contact between said first junction point and said line L;
 vi) means for connecting said electrical receptacle between said line N and a second junction point; and
 vii) means for connecting said contact means of said contactor between said second junction point and said line L; and
(g) automatically disconnecting electric current delivered to said low thermal storage device responsive to said alarm signal.

5. Apparatus in accordance with claim 1, wherein said electrical enclosure has an internal volume that is at least two orders of magnitude less than the volume of the control house in which it is to be located.

* * * * *